United States Patent [19]

Stackman et al.

[11] Patent Number: 4,554,377

[45] Date of Patent: Nov. 19, 1985

[54] PRODUCTION OF N-VINYL CARBOXYLIC ACID AMIDES

[75] Inventors: Robert W. Stackman, Morristown, N.J.; Richard H. Summerville, deceased, late of W. Orange, N.J.; James E. Summerville, Jr., heir, Signal Mountain, Tenn.

[73] Assignee: Celanese Corporation, New York, N.Y.

[21] Appl. No.: 631,047

[22] Filed: Jul. 16, 1984

[51] Int. Cl.$^4$ ................. C07C 103/133; C07C 102/00
[52] U.S. Cl. ..................................... 564/205; 564/215
[58] Field of Search ................................ 564/205, 215

[56] References Cited

U.S. PATENT DOCUMENTS

| | | | |
|---|---|---|---|
| 3,526,620 | 9/1970 | Bestian et al. | 564/215 X |
| 3,531,471 | 9/1970 | Hartwimmer et al. | 564/215 X |
| 3,763,236 | 10/1973 | Eck et al. | 564/215 X |
| 3,914,304 | 10/1975 | Schnabel et al. | 564/215 |
| 4,322,271 | 3/1982 | Jensen et al. | 564/215 X |
| 4,334,097 | 6/1982 | Schmidt | 564/215 X |

Primary Examiner—Paul F. Shaver
Attorney, Agent, or Firm—Depaoli & O'Brien

[57] ABSTRACT

The invention relates to the preparation of N-α-alkoxyethyl-carboxylic acid amides from dimethyl acetal and a carboxylic acid amide such as acetamide and to the preparation of secondary N-vinyl carboxylic acid amides such as N-vinyl acetamide therefrom.

The reaction of dimethyl acetal and the carboxylic acid amide involves an equilibrium disproportionation wherein excess dimethyl acetal is used in sufficient amounts, e.g., in a molar ratio of from about 2 to 60:1 mole ratio, so as to force the equilibrium to the desired N-α-alkoxyethyl-carboxylic acid amide intermediate product. Equilibrium is reached in about 0.1 to 150 hours at a temperature about 0° to 100° C. The intermediate N-α-alkoxyethyl-carboxylic acid amide is pyrolyzed in accordance with a known pyrolysis reaction so as to obtain the corresponding N-vinyl acetamide.

13 Claims, No Drawings

PRODUCTION OF N-VINYL CARBOXYLIC ACID AMIDES

BACKGROUND OF THE INVENTION (1) Field of the Invention

This invention relates to the preparation of N-α-alkoxyethyl-carboxylic acid amides from dimethyl acetal and a carboxylic acid amide such as acetamide and to the preparation of secondary N-vinyl carboxylic acid amides such as N-vinyl acetamide therefrom.

(2) Description of the Prior Art

Gless et al, U.S. Pat. No. 4,018,826 relates to a process for preparing poly(vinyl amine) salts. An intermediate product is N-vinyl acetamide which is obtained via the following steps:

(a) reacting acetaldehyde with at least two stoichiometric equivalents of acetamide in the presence of a strong acid catalyst to yield ethylidene-bis-acetamide;

(b) decomposing the ethylidene-bis-acetamide in the presence of an inorganic oxide surface catalyst under essentially neutral pH conditions to yield a decomposition product; and (c) separating N-vinyl acetamide from this decomposition product.

These reactions can be illustrated by the following schematic:

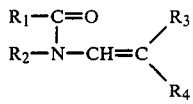

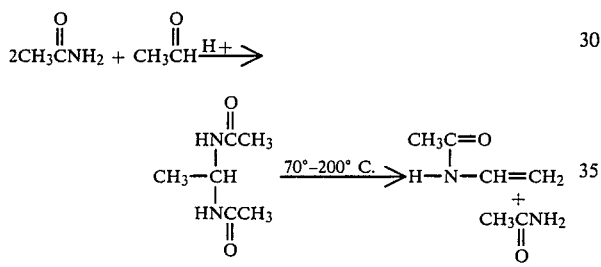

The final reaction mixture, i.e., the mixture of N-vinyl acetamide with acetamide, contains relatively poor yields of the desired N-vinyl acetamide and requires extensive purification to isolate the N-vinyl acetamide.

Hartwimmer et al, U.S. Pat. No. 3,377,340, relates to a process wherein N-vinyl compounds of the general formula:

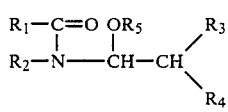

in which $R_1$ and $R_2$ each represents an alkyl group or $R_1$ and $R_2$ can be linked with each other as a ring while forming an alkylene group which may be substituted by alkyl groups, and $R_3$ and $R_4$ represent hydrogen atoms or alkyl groups, can be prepared by catalytic splitting of N-(α-alkyoxyalkyl)-compounds of the general formula:

$$R_1-C=O \quad OR_5 \quad R_3$$
$$R_2-N-\!\!-\!\!CH-CH\diagdown R_4$$

in which $R_1$, $R_2$, $R_3$ and $R_4$ have the meanings given above and $R_5$ represents an alkyl group, by heating them in liquid phase in the present of surface-active, insoluble substances which promote a weakly acid reaction.

The N-(α-alkoxyalkyl)-compounds disclosed as starting compounds can be prepared by reacting open chain or cyclic carboxylic acid amides which carry at least 1 hydrogen atom capable of being substituted on the nitrogen atom, with acetals or hemiacetals the aldehyde component of which contains more than 1 carbon atoms, or with acetal or hemiacetal-forming components in the presence of acid catalysts. However, no disclosure is made of the preparation of the specific N-vinyl amides of this invention, the specific intermediate ether amides from which they are obtained, or the critical disproportionation reaction to produce such intermediates.

SUMMARY OF THE INVENTION

According to this invention, secondary N-vinyl carboxylic acid amides having the formula:

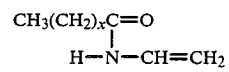

where x is 0 or an integer up to and including 9 are prepared by a novel process comprising reacting dimethyl acetal with a carboxylic acid amide having the formula

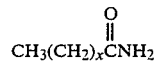

wherein x is as defined above, in the presence of an acid catalyst. The reaction involves an equilibrium disproportionation and the crux of the invention resides in the use of excess dimethyl acetal in sufficient amounts, for example, in a molar ratio of from about 2 to 60:1 mole ratio, particularly from about 10 to 30:1 mole ratio, and preferably about a 20:1 mole ratio, so as to force the equilibrium to the desired N-α-alkoxyethylcarboxylic acid amide intermediate product. Equilibrium is reached in about 0.1 to 150 hours, preferably about 0.5 to 36 hours at a temperature about 0° to 100° C., preferably 40° to 70° C. The intermediate N-α-alkoxyethyl-carboxylic acid amide is pyrolyzed in accordance with a state-of-the-art pyrolysis reaction so as to obtain the desired product.

DESCRIPTION OF THE INVENTION

The present invention relates to the production of secondary N-vinyl carboxylic acid amides having the formula

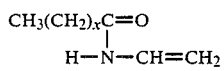

wherein x is 0 or an integer up to and including 9. The preferred products are N-vinyl acetamide and N-vinyl propionamide. In another aspect of the invention, dimethylacetal is reacted with a carboxylic acid amide having the formula

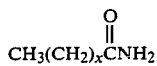

wherein x is 0 or an integer up to and including 9. The preferred starting amides are acetamide and propionamide.

The present invention comprises two process stages, the first is an equilibrium reaction of dimethyl acetal with the acid amide and the second is the pyrolysis of the intermediate ether amide. The first stage can be illustrated by the following equilibrium reaction which utilizes dimethylacetal and acetamide as starting materials. It is to be understood that the use of acetamide is for illustrative purposes only and should not be interpreted to restrict the scope of the starting materials contemplated herein. The first stage of the present process can be set forth by the following equilibrium reaction:

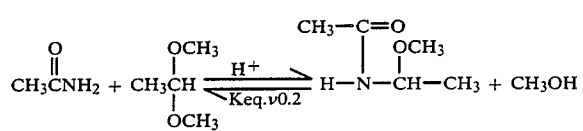

The complicating equilibrium disproportionation of the above reaction is as follows:

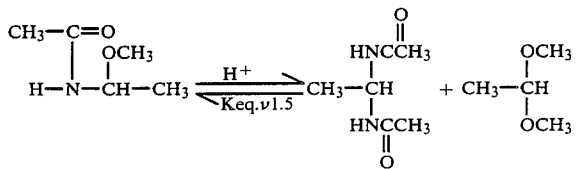

Recognition of this disproportionation is important to the instant invention. The ethylidene-bis-acetamide is highly insoluble in aprotic solvents but it is soluble in dimethyl acetal to the extent of about 2 to 3 grams per liter at 60° C. If the concentration of the N-α-methoxyethyl acetamide is sufficient, the equilibrium reaction proceeds to the right as the ethylidene-bis-acetamide crystallizes from solution. A small amount of methanol with the dimethyl acetal will, however, solubilize the ethylidene-bis-acetamide. Thus the ethylidene-bis-acetamide will remain in solution with methanol from the main reaction or with extraneous methanol present. An excess of dimethyl acetal solvent will drive the equilibrium equation to the left so that the ethylidene-bis-acetamide will not be present in significant amounts.

The equilibrium reaction is, however, also highly sensitive to the methanol concentration in that any extra methanol generates acetamide as an undesirable impurity in the ether amide. Acetamide is difficult to remove, either at this stage of the process or from the N-vinyl acetamide product after the pyrolysis stage. Production of the N-α-methoxy-ethyl acetamide by this reaction, therefore, requires balancing the two equilibria: enough methanol must be present to prevent ethylidene-bis-acetamide from precipitating but not enough to keep all the acetamide from reacting.

The conditions necessary for maintaining the desired dilute solutions comprises the uses of excess dimethyl-acetal in molar ratios of from about 2 to 60:1 mole ratio, in relation to the carboxylic acid amide. Particularly suitable are molar ratios of from 10 to 30 and preferably about a 20:1 mole ratio. Equilibrium is usually reached in about 0.1 to 150 hours, preferably in about 0.5 to 36 hours with 2 hours being especially suitable. Acid catalysts, either dissolved or undissolved in the reaction medium, are employed. As examples, the following can be considered: inorganic acids, such as hydrochloric acid or sulfuric acid, aliphatic or aromatic sulfonic acids, especially methane sulfonic acid or p-toluene sulfonic acid, halogenated aliphatic acids, such as trifluoroacetic acid, etc. The acid catalysts can be in any form, such as liquid or solid, for example, as an ion exchange resin. Temperatures utilized range from about 0° to 100° C., preferably 40° to 70° C. with about 60° C. being especially suitable.

Other acetals will exchange with acetamide, but dimethylacetal offers distinct advantages inasmuch as it is an excellent solvent. Precipitation of ethylidene-bis-acetamide becomes more of a problem utilizing acetals of higher alcohols. The low molecular weight of dimethyl acetal gives it the largest number of moles per given weight, thus allowing the carboxylic acid amide, e.g., acetamide, concentration to be higher on a weight basis. Its low boiling point allows dimethyl acetal to be readily distilled from the reaction product mixture.

As mentioned above, the second stage of the process of the present invention comprises the pyrolysis of the N-α-alkoxyethyl-carboxylic acid amide resulting from the equilibrium disproportionation reaction discussed above.

The pyrolyis of the N-α-alkoxyethyl-carboxylic acid amide is conducted essentially as that reaction disclosed in U.S. Pat. No. 3,914,304 to Schnabel et al which is incorporated herein by reference. The processes provided therein for preparing secondary N-vinyl carboxylic acid amides by heating N-α-alkoxyethyl-carboxylic acid amides in a gaseous state to temperatures from about 300° C. to 600° C., by condensing the gas mixture formed in this process while rapidly cooling and by isolating in a known manner the N-vinyl carboxylic acid amides from a condensate. The N-α-alkoxyethyl-carboxylic acid amides are dissociated into the corresponding compounds by heating them in a liquid or gaseous state to temperatures, where the desired dissociation takes place quantitatively or almost quantitatively. These temperatures are generally in the range of from 300° C. to 600° C., preferably of from 330° C. to 500° C. The dissociation is advantageously carried out as follows: The starting material is evaporated and conducted in a gaseous state into a heated reaction zone, a suitable reactor. Reactors of any design wherein the required reaction condition can be realized, may be used, for example a reaction chamber or a spherical reactor. A preferred reactor however is a reaction tube, into which the starting product is introduced at one end and where the dissociation mixture consisting of the corresponding N-vinyl carboxylic acid amide and the separated alcohol leaves at the other end. The reaction may also be carried out in the presence of an inert gas, as for example, nitrogen, argon or carbon dioxide. It may take place at atmospheric or subatmospheric pressure. The starting material is advantageously evaporated under about the same pressure under which the dissociation takes place.

The dimensions of the reaction zone are not critical, if it is guaranteed that the whole gas is heated to the reaction temperature while passing through the zone.

The average time of direct contact in the reaction zone is such that the N-α-alkoxyethyl-carboxylic acid amide is dissociated completely or nearly completely to N-vinyl-carboxylic acid amide and alcohol. At higher temperatures as well as in the case of an increasing proportion of inert gas the time of direct contact is shorter than at lower temperatures. The time of direct contact depends on the parameters of temperature, pressure, proportion of inert gas as well as the amount of reactant put through and is generally in the range of from 0.01 to 20 sec. according to the reaction conditions, but the upper limit may be exceeded. it is advantageously in the range of from 0.1 to 10 sec.

An empty, heated reactor provided with an inlet and an outlet, especially an empty tube, can be used as reaction zone, where the reaction according to the invention can be effected. For a better heat transfer, however, a reaction zone charged with a packing material can be used as well. Although simple flint stones may readily serve, packing materials made from an inert material, for example as used in the distilling technique, are advantageously used. Suitable examples include those made from glass, quartz, ceramics, porcelain, carbon, or graphite, steel, steel alloys, chromium, silver or another noble metal. The usual ring- or saddle-shaped packing, for example of glass, porcelain, preferably of steel or stainless steel are especially suitable. Compressed zinc oxide, zirconium oxide, thorium oxide, cerium oxide, chromium oxide, silicium dioxide, magnesium oxide, aluminium oxide, aluminium phosphate or calcium carbonate can be used as well, the latter however may partly cause the formation of by-products. The packing material may also consist of an acid material or acid resistant material may be coated or combined in some other way with an acid material. Acid substances on an inert porous carrier, such as pumice stone or diatomaceous earth can be used. Acid substances for the purpose of the invention are acids which are not or only slightly volatile at the temperature used, for example, pyrophosphoric acid or polyphosphoric acids. Acid salts or salts yielding acid solutions on hydrolyzing, as for example sodium hydrogen sulphate, alums, cobalt or zinc chloride, may also be used. Packing made of acid materials are less preferred in comparison with the first mentioned solid packing because they may partially cause the formation of by-products.

After leaving the reaction zone the reaction gases are cooled to temperatures of less than 70° C., preferably of less than 50° C., sufficiently rapidly so that no recombination, if possible, or only a little recombination of the dissociation products to the starting material takes place. It is especially advantageous in this process to rapidly pass the range between the condensation temperature and final temperature. This cooling process lasts for less than 5 sec., especially for less than 1 sec. and is carried out as follows: The reaction gases are introduced into a condenser or a receiver cooled to temperatures of less than 0° C., preferably less than −10° C. and more preferably less than −20° C. The cooling may also be carried out by introducing an optionally cooled inert liquid into the reaction gases through a nozzle or by introducing the reaction gases into a cooled inert liquid (quenching). Care should be taken that the liquids used for this purpose do not decompose when leaving the furnace, even at the high temperatures, or react with the sensitive N-vinyl carboxylic acid amides. Especially suitable cooling media for quenching are aprotic liquids having low solidification points. Hydrocarbons having a chain length of from 5 to 12 carbon atoms as for example petroleum ether, gasoline fractions, kerosine etc. are advantageously used in a pure form or as mixtures. Toluene, xylene, inert lower halohydrocarbons or liquid nitrogen or dry ice are also suitable.

The reaction mixture is worked up in known manner, for example by distilling off the alcohol separated in the reaction under reduced pressure and by optionally purifying the N-vinyl carboxylic acid amide, for example by distilling or crystallizing from a solvent. If a liquid is used for quenching, the reaction mixture is worked up by distilling off this liquid and the separated alcohol or, if a liquid is used, wherein the desired product is not or difficulty soluble, by filtration.

SPECIFIC EMBODIMENTS

EXAMPLE I

Preparation of N-α-Methoxy-Ethyl Acetamide

A 2 liter flask equipped with a reflux condenser and magnetic stirrer was charged with dimethyl acetal (900 grams, 10 mol), dry acetamide (30 grams, 0.5 mol) and methanesulfonic acid, 2 grams. The mixture was refluxed for 2 hrs., at which time it was cloudy but contained little solid. The solution was neutralized while still warm by filtering through potassium carbonate or Florisil (50 grams). The solvent was flash distilled under aspirator pressure into a receiver cooled in dry ice. The residue, suitable for pyrolysis, was 48–54 grams (80–90%). The recovered solvent was left to stand over 120 grams of 4A molecular sieves and could be used again the next day.

Preparation of N-Vinyl Acetamide

The pyrolysis apparatus consisted of a 250 ml 3-neck flask for vaporization immersed in an oil bath at 150° (fitted with a nitrogen inlet, a dropping funnel, a magnetic stirrer and an outlet to the pyrolysis tube); a quartz (20 inch×1inch) pyrolysis tube (packed with stainless steel shavings and heated to 580° C. with a heating tape); and two traps, the first in ice-water and the second in CO₂ acetone. The internal pressure was 7–10 mm and the internal nitrogen flow was ~1 liter/min. (~10 ml/min. at 1 atm). The N-α-methoxy-ethyl acetamide was added to the vaporization flask in small (25 grams) portions to prevent the disproportionation that sometime occurred with larger quantities being heated longer times. The N-α-methoxy-ethyl acetamide evapoarated and passed through the pyrolysis tube at ~1 gram/min. In a typical run 103 grams of N-α-methoxy-ethyl acetamide gave 3.5 grams of residue and 72 grams of N-vinyl acetamide. The residues in the two traps were combined, diluted with 75 ml of MeOH, treated with 1 gram of activated charcoal. The methanol was evaporated and the residue distilled 79°–80° at 1.7 mm to give 71 grams of white crystals (95%).

EXAMPLE 2

Preparation of N-α-Methoxy-Ethyl Acetamide

To a 250 ml 3-neck flask with reflux condenser and magnetic stirrer was added 5 grams acetamide (0.085 mol), 35 grams dimethyl acetal (0.39 mol) and Rexyn 101, a commercially available acid ion exchange resin (washed with methanol prior to use). The mixture was allowed to stir for 5 days at room temperature. At the end of this period the mixture was filtered and the excess solvent was removed by evaporation. The residue was dissolved in ethyl ether and shortly crystals formed and precipitated. The mixture was filtered and the solvent removed by evaporation to give 6.5 grams of an oily residue which was predominately the desired product (theoretical yield of N-α-methoxy-ethyl acetamide=8.6 grams).

EXAMPLE 3

Example 2 was repeated with the exception that the reaction mixture was heated to 60° C. At the end of 2 hours the mixture was filtered and the solvent removed by filtration, ether was added, the by-product crystallized out and 5.5 grams of residue recovered which was predominantely N-α-methoxy-ethyl acetamide.

EXAMPLE 4

The procedure of Example 1 was repeated except 120 grams acetamide (2.03 moles) and 1200 grams dimethyl acetal (13.3 moles) were used and the catalyst was 10 grams of Rexyn 101, a commercially available acid exchange resin/washed with methanol. The mixture was stirred for 5 days. The solvent was removed by evaporation, dissolved in ether, and allowed to form crystals. The ether solution was filtered and evaporated to give 98 grams of product (42%).

EXAMPLE 5

The procedure of Example 4 was repeated except that 1 gram of concentrated sulfuric acid was used as catalyst (instead of Rexyn 101). After 3 days at room temperature the reaction mixture was worked up to give 174 grams of product (85% yield).

EXAMPLES 6-8

Effect of Dimethyl Acetal to Acetamide Ratio

The procedure of Example 3 was repeated with the following quantities of dimethyl acetal and acetamide.

the pyrolysis tubes. The recovery of N-vinyl propionamide from the tubes amounted to 26 grams (90%).

EXAMPLE 11

Effect of Added Ethanol to Dissolve Bis-Acetamide

To a 500 ml flask with magnetic stirrer and reflux condenser was added 30 grams acetamide (0.50 mol), 23 grams absolute ethanol and 295 grams dimethyl acetal (3.28 moles). The mixture was heated to reflux and all the solids dissolved. One gram of methane sulfonic acid was added with rapid stirring. The progress of the reaction was monitored by use of thin layer chromatography to determine the ratio of ethylidene bis-acetamide to N-α-methoxy-ethyl acetamide. After 45 minutes at reflux, equilibrium was attained and the mixture neutralized with potassium carbonate. A 3:1 N-α-methoxy-ethyl acetamide to ethylidene bis-acetamide ratio was obtained.

When the reaction is repeated without the addition of ethanol the ratio of N-α-methoxy-ethyl acetamide to ethylidene bis-acetamide was 3.6:1 with a 90% yield of the desired product.

EXAMPLE 12

Effect of Added Methanol to Dissolve Bis-Acetamide

To a 500 ml flask with reflux condenser was added 30 grams acetamide (0.5 mol) and 225 grams dimethyl acetal (2.5 moles). The mixture was heated to reflux and most of the solids dissolved. One gram of methane sulfonic acid was added. After 15 minutes all of the solids had dissolved after 24 hours refluxing a large amount of precipitate (identified as ethylidene bis-acetamide) had formed. Thirty-two milliliters of methanol was added and the solids dissolved. The reflux was continued for an additional 6 hours at which time the ratio of N-α-methoxy-ethyl acetamide to ethylidene bis-acetamide (as determined by thin layer chomatography) was 1.8:1.

|  | Example 6 | Example 7 | Example 8 |
| --- | --- | --- | --- |
| Acetamide | 7.5 g (0.125 mol) | 15.0 g (0.25 mol) | 30 g (0.50 mol) |
| Dimethyl acetal | 225 g (2.5 moles) | 225 g (2.5 moles) | 225 g (2.5 moles) |
| Dimethyl acetal / acetamide | 20 | 10 | 5 |
| Catalyst | Methane Sulfonic Acid | Methane Sulfonic Acid | Methane Sulfonic Acid |
| Reaction Temp. °C. | 60° | 60° | 60° |
| Reaction Time °C. | 3 hrs. | 3 hrs. | 3 hrs. |
| Yield (N—α-methoxy-ethyl acetamide | 14 g | 15.3 g | 29.5 g |
| % yield (based on acetamide) | 96% | 53% | 50% |

EXAMPLE 9

Preparation of N-α-Methoxy-Ethyl Propionamide

The procedure in Example 1 was followed with the exception that the following reactants were used:
dimethyl acetal 900 grams (10 moles)
propionamide 37 grams (0.5 mol)
The recovered N-α-methoxy-ethyl propionamide amounted to 49 grams (75% yield).

EXAMPLE 10

Preparation of N-Vinyl Propionamide

The procedure in Example 2 was repeated except that instead of N-α-methoxy-ethyl acetamide, 40 grams of N-α-methoxy-ethyl propionamide was passed through Yield of N-α-methoxy-ethyl acetamide was 27 grams (53%).

The reaction was repeated with the use of 15 grams (0.25 mol) of acetamide and 225 grams (2.5 moles) of dimethyl acetal. Five milliliters of methanol were used and a 16% yield of N-α-methoxy-ethyl acetamide was obtained. The ratio of N-α-methoxy-ethyl acetamide to ethylidene bis-acetamide was 5:1.

Repeating the above reaction the methanol gave a 92% yield of the desired N-α-methoxy-ethyl acetamide.

What is claimed is:

1. A process for the preparation of N-α-alkoxy-ethyl-carboxylic acid amides which comprises reacting dimethyl acetal in the presence of an acid catalyst with a carboxylic acid amide having the formula:

$$\underset{\text{CH}_3(\text{CH}_2)_x\overset{\overset{\displaystyle O}{\|}}{\text{C}}\text{NH}_2}{}$$

wherein x is 0 or an integer up to and including 9 and wherein the molar ratio of dimethyl acetal to carboxylic acid amide is from about 2 to 60:1 to produce an N-α-alkoxy-carboxylic acid amide.

2. The process of claim 1 wherein the molar ratio of dimethyl acetal to carboxylic acid amide is from about 10 to 30:1.

3. The process of claim 1 wherein the molar ratio of dimethyl acetal to carboxylic acid amide is about 20:1.

4. The process of claim 1 wherein the reaction is carried out for a period of from about 0.1 to 150 hours, preferably 0.5 to 36 hours.

5. The process of claim 1 wherein the reaction is carried out at a temperature of about 0° to 100° C., preferably from about 40° to 70° C.

6. A process for the preparation of secondary N-vinyl carboxylic acid amides having the formula:

$$\text{CH}_3(\text{CH}_2)_x\underset{\underset{\displaystyle \text{H}-\text{N}-\text{CH}=\text{CH}_2}{|}}{\text{C}=\text{O}}$$

wherein x is 0 or an integer up to and including 9 which comprises reacting dimethyl acetal in the presence of an acid catalyst with a carboxylic acid amide having the formula:

$$\underset{\text{CH}_3(\text{CH}_2)_x\overset{\overset{\displaystyle O}{\|}}{\text{C}}\text{NH}_2}{}$$

wherein x is as defined above, and wherein the molar ratio of dimethyl acetal to carboxylic acid amide is from about 2 to 60:1 to produce an intermediate N-α-alkoxyethyl-carboxylic acid amide and pyrolyzing said N-α-alkoxyethyl-carboxylic acid amide to obtain the corresponding N-vinyl carboxylic acid amide.

7. The process of claim 6 wherein the molar ratio of dimethyl acetal to carboxylic acid amide is from about 10 to 30:1.

8. The process of claim 6 wherein the molar ratio of dimethyl acetal to carboxylic acid amide is about 20:1.

9. The process of claim 6 wherein the reaction is carried out for a period of from about 0.1 to 150 hours, preferably 0.5 to 36 hours.

10. The process of claim 6 wherein the reaction is carried out at a temperature of about 0° to 100° C., preferably from about 40° to 70° C.

11. The process of claim 6 wherein the pyrolysis is conducted in the gaseous state a temperature from about 300° to 600° C.

12. The process of claim 6 wherein the carboxylic acid amide is acetamide or propionamide.

13. The process of claim 6 wherein the carboxylic acid amide is acetamide.

* * * * *